United States Patent [19]

Kragten et al.

[11] Patent Number: 5,319,146
[45] Date of Patent: Jun. 7, 1994

[54] ALKYL PEROXIDES AND USES

[75] Inventors: Ubaldus Kragten, Beek; Otto E. Sielcken, Sittard, both of Netherlands

[73] Assignee: DSM N.V., Netherlands

[21] Appl. No.: 995,745

[22] Filed: Dec. 22, 1992

[30] Foreign Application Priority Data

Dec. 23, 1991 [BE] Belgium ............... 9101177

[51] Int. Cl.$^5$ ............................. C07C 409/14
[52] U.S. Cl. ............................. 568/558
[58] Field of Search ............... 568/558, 570

[56] References Cited

U.S. PATENT DOCUMENTS 2,668,180  2/1954  Boardman ............. 568/558
3,267,066  8/1966  Tyssen ................. 568/558

FOREIGN PATENT DOCUMENTS 0128536  5/1979  Japan .

*Primary Examiner*—Werren B. Lone
*Attorney, Agent, or Firm*—Cushman, Darby & Cushman

[57] ABSTRACT

The invention relates to a compound having the Formula (I)

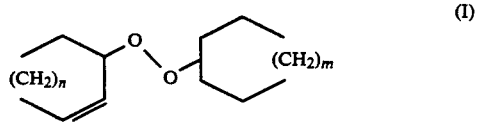

(I)

in which n=1, 2, 3 or 4 and m=1, 2, 3, 4, 5, 6, 7 or 8.

The invention also relates to a method for the preparation of the above-described compound by bringing a cycloalkyl hydroperoxide having 5 to 12 carbon atoms into contact with a cycloalkene having 5-8 carbon atoms, under the influence of a metal compound as catalyst, the metal being chosen from groups VIB, VIIB and VIII of the periodic system. The reaction takes place at a temperature of 0°–80° C.

19 Claims, No Drawings

ALKYL PEROXIDES AND USES

BACKGROUND OF THE INVENTION

1. Technical Field

The invention relates to alkyl peroxides and uses thereof.

2. Background Information

Alkyl peroxides are described, for example, in EP-A-174194. In particular, in this publication t-butylcyclohexyl peroxide is produced as a byproduct of a cyclohexane oxidation with t-butyl hydroperoxide. The peroxide is produced with a selectivity of less than 50%.

Peroxides are widely used as free radical initiators, and there is a continuous demand for new peroxides. Thus, in EP-A-322945, alkenyl-alkyl peroxides are described which are used for the modification of saturated thermoplastic polymers.

SUMMARY OF THE INVENTION

It has now been found that a specific new category of peroxides can be produced with a relatively high yield. The compounds concerned have the Formula I

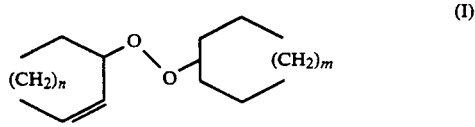

in which
n=1, 2, 3 or 4 and
m=1, 2, 3, 4, 5, 6, 7 or 8.

Preferably, n is 1 or 2 because these peroxides, according to the invention, can be obtained in a very high yield.

m is preferably 2, 4 or 8 because cyclohexyl hydroperoxide, cyclooctyl hydroperoxide and cyclododecyl hydroperoxide are readily available because of the preparation of epsilon-caprolactam, omega-octyl lactam and omega-dodecyl lactam.

All U.S. patents and publications referred to herein are hereby incorporated by reference.

DETAILED DESCRIPTION OF THE INVENTION

The peroxides according to the invention can be produced with a particularly high yield by bringing a cycloalkene having 5-8 carbon atoms into contact at 0°-80° C. with a cycloalkyl hydroperoxide having 5-12 carbon atoms, in the presence of a metal catalyst, the metal being chosen from groups VIB, VIIB and VIII of the periodic system. The metal must have a sufficient activity for the desired reaction. Metals which, for example, usually give epoxidation reactions can, as a rule, not be used. Preferably, Mn, Co or Cr, and more particularly, Mn or Co, are used.

In principle, the metal has a satisfactory action if it is present in the medium in a finely divided state, preferably dissolved. For example, manganese oxide particles, or metal complexes with organic ligands, can be used.

The ligand used is preferably a phthalocyanine, porphyrin, salene (salicylideneaminophenol) or acetate group, in order to keep the metal readily soluble. The ligand makes the relatively polar metal more apolar and, thus, more soluble in an apolar organic solution such as a mixture of cycloalkylhydroperoxide and cycloalkene.

If phthalocyanine is used, the reaction is preferably carried out in the presence of a quinone compound, in combination with a compound containing an imidazole group or another compound containing aromatic nitrogen. Examples of these latter two types of compounds include imidazole, pyridines and isoquinolines.

The alkenyl-alkyl peroxides described in EP-A-322945 are peroxides in which the alkyl group must always have a tertiary carbon atom. The tertiary carbon atom forms a bond with oxygen. In addition, these peroxides are prepared in a totally different way. Furthermore, it is known per se to allow cycloalkenes to react with hydroperoxides, as, for example, described in U.S. Pat. No. 3,931,249, but in this case essentially epoxides are formed, while by-products have not been characterized. In contrast, using the method according to the invention, as a rule less than 10%, and frequently even less than 5% of epoxide is formed. This is advantageous, because, as a result, the ethylenic unsaturation remains intact.

In particular, in U.S. Pat. No. 3,931,249, the following reaction occurs:

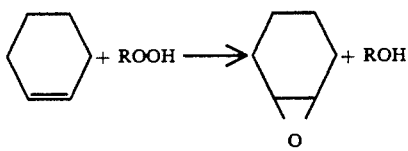

In contrast, in the claimed invention, the following reaction occurs:

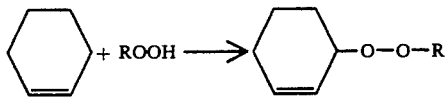

The ethylenic unsaturation is advantageous when the compound is used for the modification of saturated thermoplastic polymers because, after polymerization, the compound can easily become part of the polymer matrix.

The cycloalkenyl-cycloalkyl peroxide formed according to the invention, but also the reaction mixture obtained, can be used for the production of alkylenically unsaturated alcohols and/or alkanones. On the one hand, a certain amount of cycloalkenone and cycloalkenol is formed already during the preparation, and, on the other hand, the cycloalkenyl-cycloalkyl peroxide can be decomposed to give cycloalkenol and optionally cycloalkenone. The alkenone/alkenol mixture obtained can (preferably after separating off the alcohol originating from the alkyl part) be purified to give pure alkenone, which can be converted, via oxime formation and a Beckmann rearrangement, to give the unsaturated lactam.

Partly because it is carried out under very mild conditions, the method according to the invention can also be used for the preparation of saturated lactams. In this case, the group chosen as the cycloalkyl group of the cycloalkyl hydroperoxide is preferably a group which is the saturated analogue of the cycloalkene. Thus, for example, cyclohexene is preferably combined with cyclohexyl hydroperoxide. The mixture of alkenyl-alkyl peroxide, alkenone, alkenol, alkanol and, where appropriate alkanone formed using the method according to the invention, can then be treated directly or in a subsequent step in order to allow the peroxide to decompose.

This can be effected, for example, by hydrogenation, the ethylenic unsaturations also being hydrogenated then. For example, the peroxide can be hydrogenated under the influence of palladium-on-charcoal, Raney nickel or Raney cobalt and hydrogen or, optionally, sodium borohydride. The mixture obtained after hydrogenation consists mainly of cycloalkanol and optionally cycloalkanone in cycloalkane. The cycloalkanol can be separated off in a known manner and hydrogenated to give cyclohexanone, which can be further reacted to the oxime in a known manner.

Three processes can now be integrated highly advantageously and relatively simply in the above manner. Thus, for example, in the case of integration of cyclohexane and cyclohexene as starting materials for epsilon-caprolactam preparation, a valuable cyclohexenylcyclohexyl peroxide can be obtained. In addition, provision can be made for the preparation of unsaturated lactams (which can be used for the preparation of unsaturated polyamides).

Cycloalkenes having 5–8 carbon atoms are commercially available. For example, cyclohexene can be prepared highly advantageously by partial hydrogenation of benzene. The cycloalkenes do not have to be used in the pure form. For example, solutions containing 5–40% by weight in an organic medium are very suitable. Preferably, the cycloalkene-containing solution does not contain metals in concentrations which break down a cycloalkyl hydroperoxide to be added.

The cycloalkyl peroxide can be produced in a known manner by oxidation of cycloalkane using an oxygen-containing gas mixture. In this process, air is supplied to cycloalkane at a temperature of 140°–250° C. under 4–20 at. (0.5–2 MPa), preferably without a metal catalyst, in, preferably a series of, reactors, for example, a tank reactor, by which means cycloalkyl peroxide is formed, usually in a concentration of 2–8 and preferably 4–6% by weight.

Both the cycloalkene and the cycloalkyl hydroperoxide can first be purified or concentrated, for example, by distillation or washing with water and/or alkali, before they are reacted. This is preferred, in particular, in the case of the cycloalkyl hydroperoxide.

In the method according to the invention, the reaction of the cycloalkyl peroxide with the cycloalkene takes place at a temperature of between 0° and 100° C. A higher temperature usually gives rise to secondary and subsequent reactions, such as the thermal decomposition of the alkyl peroxides and hydroperoxides and, for example, epoxidation reactions. A lower temperature gives rise to a rate of reaction which may be too slow. The reaction is preferably carried out at between 20° and 80° C.

Depending on the desired conversion, and the activity of the catalyst, the reaction takes 10 min–10 hours, preferably 30 min–3 hours.

A usable concentration of the catalyst can easily be determined by a person skilled in the art. As a rule, between 0.1 and 5 mM of catalyst per mol of hydroperoxide, preferably 0.1–1 mM, is used.

The concentration and ratio of cycloalkene and cycloalkyl peroxide are not subject to any restriction. For an economically acceptable method, the concentration of the two compounds will be greater than 1% by vol, preferably 3–40% by vol. The ratio of alkene to peroxide is, as a rule, between 1:20 and 10:1, in particular, 1:10–5:1.

The catalyst used is a finely divided metal compound or dissolved metal compound, the metal preferably being chosen from Mn, Co, Cr or mixtures thereof. In order to be readily available for the reaction, the metal compound preferably has one or more ligands, such as, for example, acetylacetonate, acetate, porphyrin, phthalocyanine or salene. However, other ligand systems are also suitable. If phthalocyanine is used, it is advantageous also to add a quinone and a compound containing aromatic nitrogen. Especially in homogeneous systems, it is advantageous to use substituted ligands in order to prevent dimerization of metals. Thus, for example, it is possible to substitute phthalocyanine by groups containing 4–10 carbon atoms, such as, for example, octyl, t-butyl, 2-ethylhexyl and cyclohexyl. The use of a substituted ligand of this type gives higher rates of reaction and a better stability to the system.

The catalyst can be homogeneously dispersed or can be applied to a support. The second heterogeneous catalyst is frequently preferred because it is simple to handle. The first catalyst usually gives higher conversions per unit time for a given concentration.

The reaction can be carried out batchwise or continuously. If the reaction is carried out continuously, the reaction mixture can be passed over a solid catalyst bed.

After the reaction, in which a mixture of preferably more than 3% by weight of cycloalkenylcycloalkyl peroxide in an organic solvent, with a little cyclo- alkanol, cycloalkenone and cycloalkenol, is finally formed, the mixture can be purified or concentrated. (The ratio of cycloalkanol, cycloalkenol and cycloalkenone to cycloalkenylcycloalkyl-peroxide is approximately 1:7.) Alternatively, it can be used directly for carrying out a subsequent reaction.

By, if necessary, distilling off a portion of the solvent, a solution containing more than 10% by weight of cycloalkenyl-cycloalkyl peroxide is preferably prepared.

Purification can be carried out, for example, in the same manner as purification of a mixture obtained after a cyclohexyl hydroperoxide decomposition. The procedure usually involves first washing the mixture with aqueous alkali, after which lightweight components, including epoxy cyclohexane, are separated off in a first distillation column. The products obtained can then be further separated by distillation, cyclohexane being recycled to a cyclohexane oxidation.

The peroxide-containing mixture can also be subjected to distillation, as long as the temperature does not rise above 100° C.

The invention will be illustrated in more detail with the aid of the following, non-limiting examples.

EXAMPLES

Example I

SAP was prepared from equimolar amounts of salicylaldehyde and aminophenol in absolute ethanol as described in Can. J. Chem. (1975), 53, pp 939–944. The manganese-SAP complex was prepared by refluxing SAP and manganese acetate in absolute ethanol, as described in Polyhedron (1986), 5, pp 271–275.

113 mg ($4 \times 10^{-4}$ mol) of manganese-SAP and 30 of 1,2-dichloroethane (analytical grade) were introduced into a 100 ml three-necked round-bottomed flask provided with a stirrer, a thermometer, a reflux condenser with a nitrogen connection, and a diaphragm for sampling. The reaction mixture was placed under a nitrogen atmosphere, after which 8.154 grams (99.3 mmol) of cyclohexene were added. The reaction mixture was heated to 50° C. 10 ml of a mixture consisting of 39.7 mmols of cyclohexyl hydroperoxide, 13.3 mmols of cyclohexanone, and 19.9 mmols of cyclohexanol in cyclohexane was then added dropwise in the course of 20 minutes. After 3 hours, the reaction mixture was cooled to room temperature. The reaction mixture still contained 8.99 mmols of cyclohexyl hydroperoxide. The conversion of cyclohexene, determined from analysis of the reaction mixture, was 81% (determined with respect to consumption of cyclohexyl hydroperoxide). The selectivity for the various reaction products was: cyclohexyl-cyclohexenyl peroxide: 67.3%; cyclohexenone 16.8%; cyclohexenol 15.1% and cyclohexene oxide <1%.

Example II

A manganese-phthalocyanine compound was prepared as described in "Phthalocyanines and Properties", C. Leznoff & A. Lever (Eds), VCH Publishers Inc., New York, (1989). The reaction was carried out in a manner analagous to that described for Example I, using a reaction mixture consisting of 100 mg ($6.3 \times 10^{-5}$ mol) of octo(octyloxymethyl)phthalocyanine-manganese(III) ($O_2$), 60 mg ($5.6 \times 10^{-4}$ mol) of 1,4-benzoquinone, 40 mg ($5.9 \times 10^{-4}$ mol) of imidazole, 8.376 g (0.1020 mol) of cyclohexene, 42.3 mmols of cyclohexyl hydroperoxide, 21.6 mmols of cyclohexanol and 14.1 mmols of cyclohexanone in 30 ml of 1,2-dichloroethane. After a reaction time of 2 hours at 50° C., 1.3 mmols of cyclohexyl hydroperoxide remained. The cyclohexene conversion: 92%; selectivity: cyclohexylcyclohexenyl peroxide 77.1%, cyclohexenone 11.5%, cyclohexenol 9.4% and cyclohexene oxide <1%.

Example III

The reaction was carried out in a manner analogous to that described for Example I, using a reaction mixture consisting of 15 mg ($8.7 \times 10^{-5}$ mol) of manganese acetate, 1.6821 g (20.5 mmol) of cyclohexene, 7.9 mmol cyclohexyl hydroperoxide, 4.0 mmol of cyclohexanol and 2.6 mmols of cyclohexanone in 6 ml of 1,2-dichloroethane. After a reaction time of 3 hours at 50° C., 2.1 mmols of cyclohexyl hydroperoxide remained. Cyclohexene conversion: 82%; selectivity: cyclohexylcyclohexenyl peroxide 69.7%, cyclohexanone 14.9%, cyclohexenol 13.1% and cyclohexene oxide <1%.

Example IV

An experiment was carried out analogously to Example II using 30 ml of cyclohexane instead of 1,2-dichloroethane. Comparable results were obtained.

Hydrogenation of Cyclohexyl-cyclohexenyl Peroxide

A mixture consisting of 8.4 mmols of cyclohexyl-cyclohexenyl peroxide, 35.7 mmols of cyclohexanol, 22.7 mmols of cyclohexanone, 1.9 mmols of cyclohexenol and 2.1 mmols of cyclohexenone was introduced into an autoclave, to which 30 ml of absolute ethanol and 5 mol % of Pd-on-active charcoal were added. The reaction was carried out under 6 bar H, and at 50° C. After 4 hours, the reaction was stopped, the catalyst was filtered off, and the ethanol was removed. $^1$H-NMR and GC analysis showed that the cyclohexylcyclohexenyl peroxide, cyclohexenol and cyclohexenone had disappeared and that only cyclohexanol (87%) and cyclohexanone (10%) were present.

What is claimed is:

1. Compound having the Formula (I) in which n=1, 2, 3 or 4 and m=1, 2, 3, 4, 5, 6, 7 or 8.

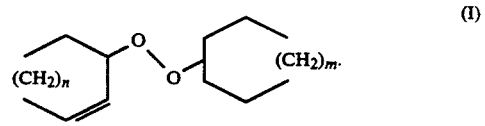

2. Compound according to claim 1, wherein n=1 or 2.

3. Compound according to claims 1 or 2, wherein m=2, 4 or 8.

4. Mixture comprising an organic solvent and at least 3% by weight of a compound according to claim 1.

5. Mixture comprising an organic solvent and more than 10% by weight of a compound according to claim 1.

6. Method for the preparation of a compound according to claim 1 comprising the step of bringing a cycloalkyl hydroperoxide having 5 to 12 carbon atoms into contact with a cycloalkene having 5-8 carbon atoms, under the influence of a metal compound as catalyst, the metal being chosen from groups VIB, VIIB and VIII of the periodic system, said contact occurring at a temperature of 0°-80° C.

7. Method according to claim 6, wherein the metal is selected from the group consisting of Mn, Co and Cr.

8. Method according to claim 7, wherein the metal compound comprises a metal bound to at least one ligand.

9. Method according to claim 8, wherein said ligand is selected from the group consisting of phthalocyanine, porphyrine and salene.

10. Method according to claim 9, wherein said ligand is a phthalocyanine and wherein a quinone compound and a compound containing aromatic nitrogen are present during said contact.

11. Method for the preparation of cycloalkenol, cycloalkenone or a mixture thereof, comprising the step of decomposing a compound according to claim 1 to yield a corresponding cycloalkenol, cycloalkenone, or mixture thereof, respectively.

12. Method for the preparation of cycloalkanol, cycloalkanone, or a mixture thereof, comprising hydrogenating a compound according to claim 1 to yield a corresponding cycloalkanol, cycloalkanone, or a mixture thereof, respectively.

13. Method for the preparation of cycloalkanol, cycloalkanone, or a mixture thereof, comprising hydrogenating a cycloalkenol, cycloalkenone or mixture thereof, obtained according to the method of claim 11, to yield a corresponding cycloalkanol, cycloalkenone, or a mixture thereof, respectively.

14. Mixture according to claim 4, wherein said mixture further comprises a cycloalkenol, a cycloalkenone, a cycloalkanol, or a combination thereof.

15. Mixture according to claim 5, wherein said mixture further comprises a cycloalkenol, a cycloalkenone, a cycloalkanol, or a combination thereof.

16. Mixture according to claim 9, wherein said ligand is a phthalocyanine and wherein said phthalocyanine is substituted by groups containing 4-10 carbon atoms.

17. Mixture according to claim 16, wherein said phthalocyanine is substituted by alkyl groups containing 4-10 carbon atoms and is selected from the group consisting of octyl, t-butyl, 2-ethylhexyl, and cyclohexyl.

18. Method for the preparation of a compound according to claim 1 comprising the step of bringing a cycloalkylhydroperoxide having 5-12 carbon atoms into contact with a cycloalkene having 5-8 carbon atoms in an organic solvent in which the concentration of the two compounds is between 3-40% by volume, and the ratio of alkene to peroxide is between 1:20 and 10:1, wherein said step is carried out in the presence of a catalytically effective amount of a metal selected from the group consisting of Mn, Co, and Cr, and said contact occurs at a temperature of 0°-80° C.

19. Method according to claim 18, wherein the metal has at least one ligand selected from the group consisting of acetylacetonate, acetate, porphyrin, phthalocyanine and salene.

* * * * *